(12) United States Patent
Hirama et al.

(10) Patent No.: US 11,067,589 B2
(45) Date of Patent: Jul. 20, 2021

(54) AUTOMATED ANALYZER

(71) Applicant: HITACHI HIGH-TECHNOLOGIES CORPORATION, Tokyo (JP)

(72) Inventors: Yoshiteru Hirama, Tokyo (JP); Tatsuya Fukugaki, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 379 days.

(21) Appl. No.: 16/083,111

(22) PCT Filed: Jan. 23, 2017

(86) PCT No.: PCT/JP2017/002048
§ 371 (c)(1),
(2) Date: Sep. 7, 2018

(87) PCT Pub. No.: WO2017/168993
PCT Pub. Date: Oct. 5, 2017

(65) Prior Publication Data
US 2019/0094253 A1 Mar. 28, 2019

(30) Foreign Application Priority Data
Mar. 28, 2016 (JP) .............................. JP2016-062975

(51) Int. Cl.
G01N 35/10 (2006.01)
G01N 35/02 (2006.01)
(Continued)

(52) U.S. Cl.
CPC ......... *G01N 35/1002* (2013.01); *G01N 35/00* (2013.01); *G01N 35/025* (2013.01);
(Continued)

(58) Field of Classification Search
CPC .. G01N 35/1002; G01N 35/00; G01N 35/025; G01N 33/50; G01N 21/64;
(Continued)

(56) References Cited

U.S. PATENT DOCUMENTS

| 5,201,348 A | 4/1993 | Lurz |
| 2001/0050276 A1* | 12/2001 | Inami ........................ B01L 7/00 219/390 |

(Continued)

FOREIGN PATENT DOCUMENTS

| EP | 1225450 A1 | 7/2002 |
| JP | 5-149957 A | 6/1993 |

(Continued)

OTHER PUBLICATIONS

International Search Report of PCT/JP2017/002048 dated May 16, 2017.

(Continued)

Primary Examiner — Kathryn Wright
Assistant Examiner — Curtis A Thompson
(74) Attorney, Agent, or Firm — Mattingly & Malur, PC

(57) ABSTRACT

An automatic analysis device is provided with a storage chamber for adjusting the temperature of and storing a container in which liquid is stored, an opening provided in a portion of the storage chamber, and a loader mechanism for bringing the container in and out of the storage chamber by moving the container through the opening, and is characterized in that the loader mechanism and storage chamber are closed by an elastic body. In the present invention, attaching a sealing member for sealing to an upper part from among overlapping parts makes it difficult for debris and dust to adhere to the sealing member and makes it possible to maintain the sealed state of a reagent storage chamber over a long period of time.

6 Claims, 14 Drawing Sheets

(51) Int. Cl.
*G01N 35/00* (2006.01)
*B01J 19/00* (2006.01)
*F27B 9/06* (2006.01)
*G01N 21/64* (2006.01)
*B01L 3/00* (2006.01)
*B67C 3/00* (2006.01)
*B65B 43/42* (2006.01)
*G01N 33/50* (2006.01)
*B23P 11/00* (2006.01)
*B65G 1/04* (2006.01)
*G01N 35/04* (2006.01)

(52) U.S. Cl.
CPC .................. *B01J 19/00* (2013.01); *B01L 3/00* (2013.01); *B23P 11/00* (2013.01); *B65B 43/42* (2013.01); *B65G 1/04* (2013.01); *B67C 3/00* (2013.01); *F27B 9/06* (2013.01); *G01N 21/64* (2013.01); *G01N 33/50* (2013.01); *G01N 35/00663* (2013.01); *G01N 35/10* (2013.01); *G01N 2035/00287* (2013.01); *G01N 2035/00306* (2013.01); *G01N 2035/00435* (2013.01); *G01N 2035/00673* (2013.01); *G01N 2035/0443* (2013.01)

(58) Field of Classification Search
CPC ... G01N 35/00663; G01N 2035/00287; G01N 35/10; G01N 2035/00673; G01N 2035/00306; G01N 2035/00435; G01N 2035/0443; G01N 2035/0465; B23P 11/00; B65G 1/04; B01L 3/00; B67C 3/00; B65B 43/42; F27B 9/06; B01J 19/00
See application file for complete search history.

(56) References Cited

U.S. PATENT DOCUMENTS

| 2007/0071645 | A1* | 3/2007 | Araki | G01N 35/00 422/65 |
| 2008/0085215 | A1* | 4/2008 | Mototsu | G01N 35/025 422/68.1 |
| 2010/0251754 | A1* | 10/2010 | Lim | F25D 23/025 62/455 |
| 2012/0047934 | A1* | 3/2012 | Park | F25D 25/024 62/264 |
| 2012/0237398 | A1 | 9/2012 | Katsumi et al. | |
| 2012/0272500 | A1 | 11/2012 | Reuteler | |
| 2012/0301359 | A1* | 11/2012 | Kraemer | G01N 35/1002 422/64 |
| 2012/0329143 | A1 | 12/2012 | Yamazaki et al. | |
| 2016/0161521 | A1* | 6/2016 | Sakairi | G01N 35/1002 422/67 |

FOREIGN PATENT DOCUMENTS

| JP | 2001-352969 A | 12/2001 | |
| JP | 2008-096201 A | 4/2008 | |
| JP | 2011-027663 A | 2/2011 | |
| JP | 2012-194071 A | 10/2012 | |
| JP | 2013-007688 A | 1/2013 | |
| JP | 2013-508237 | 3/2013 | |
| WO | 2015/025616 A1 | 2/2015 | |
| WO | WO-2015025616 A1 * | 2/2015 | ....... G01N 35/00663 |

OTHER PUBLICATIONS

Japanese Office Action received in corresponding Japanese Application No. 2018-508434 dated Jul. 30, 2019.

* cited by examiner

[FIG. 1]
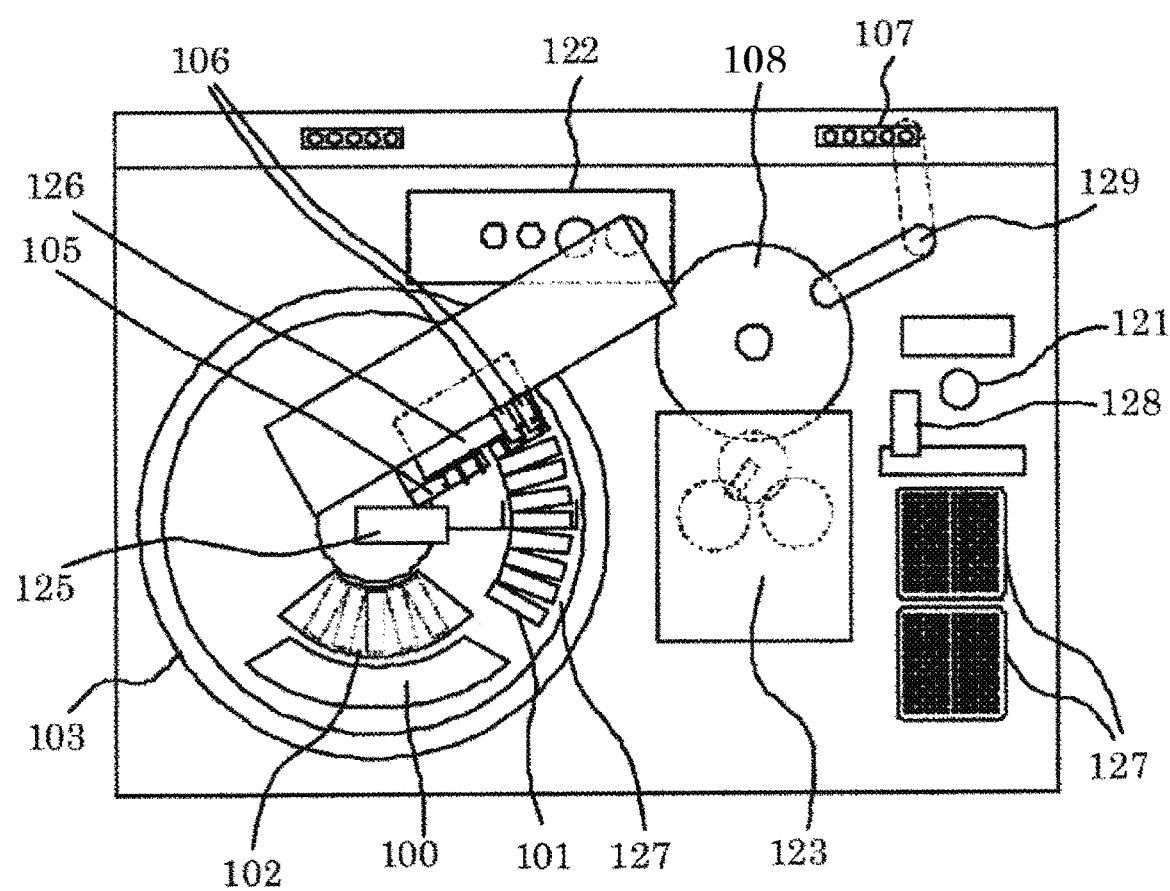

[FIG. 2]
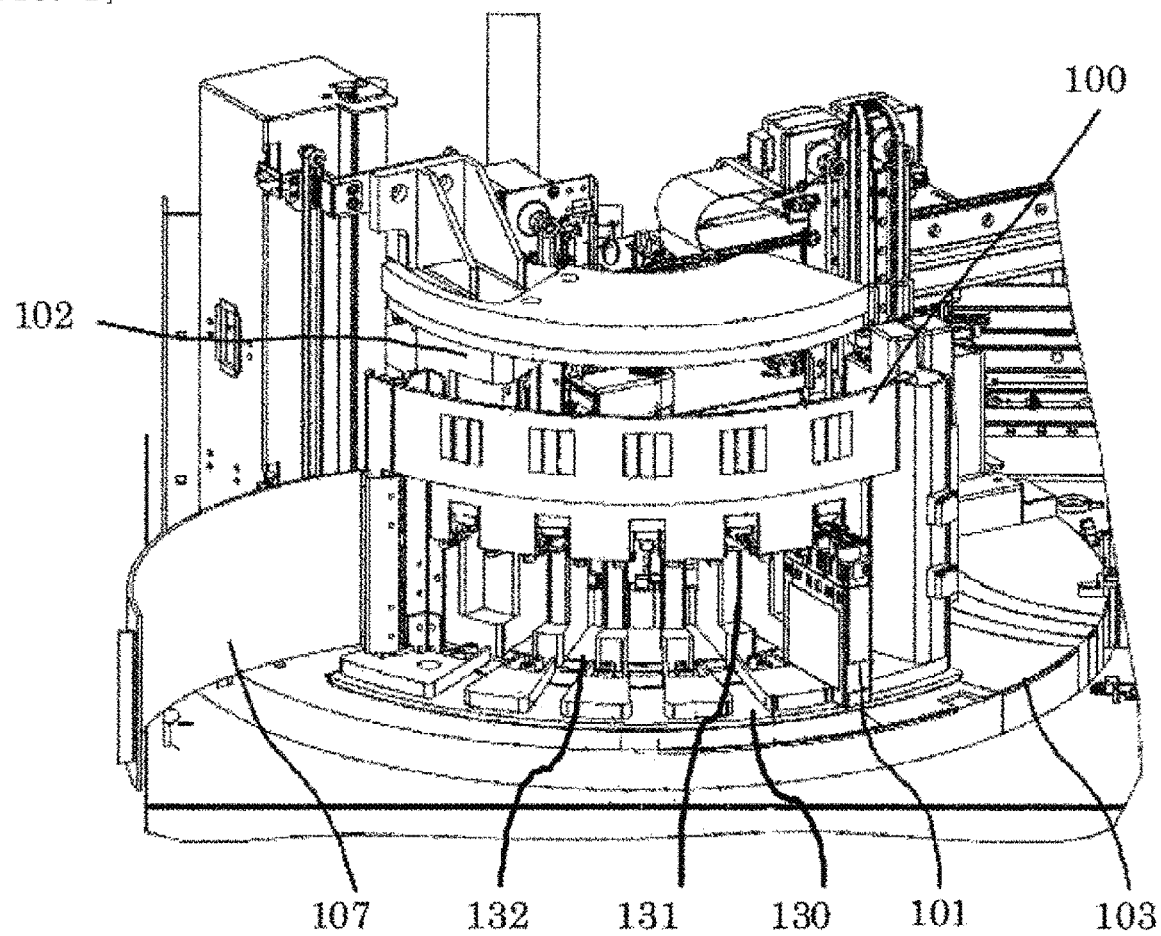

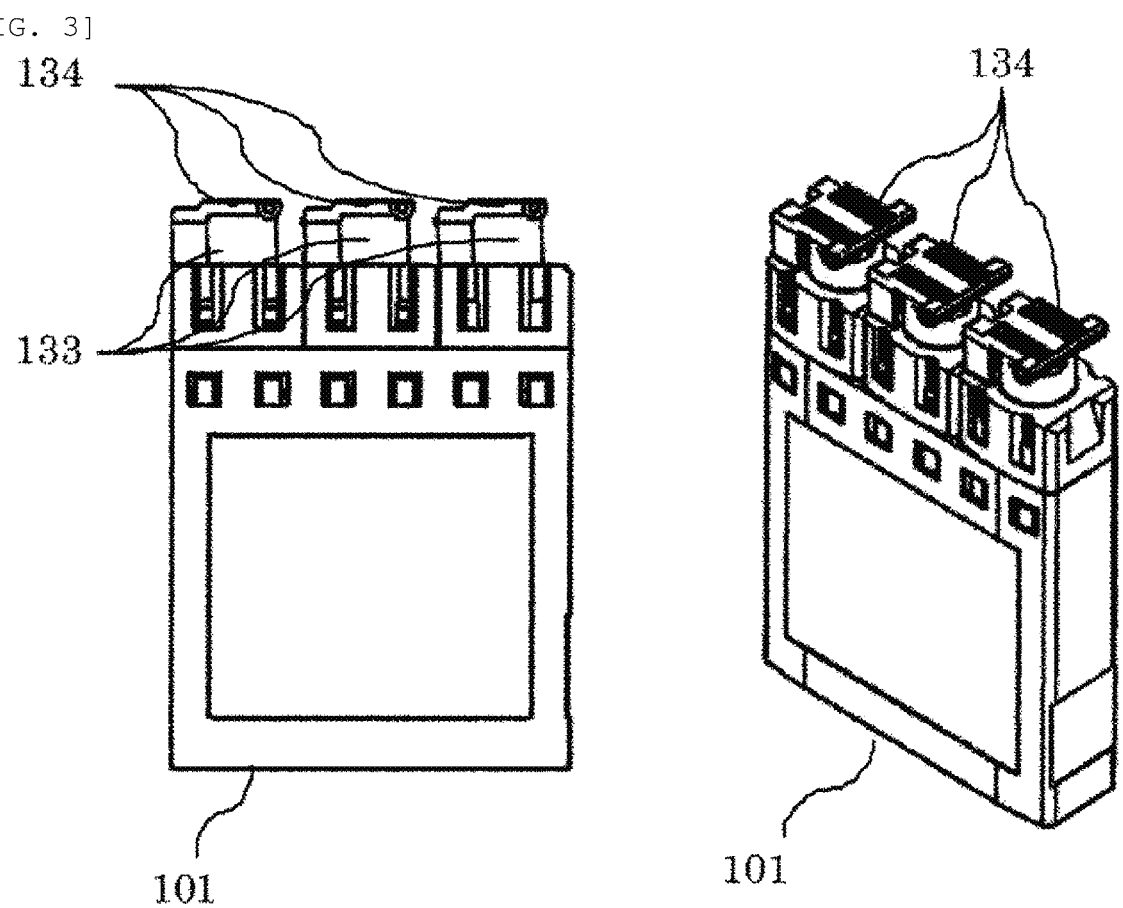

[FIG. 4]
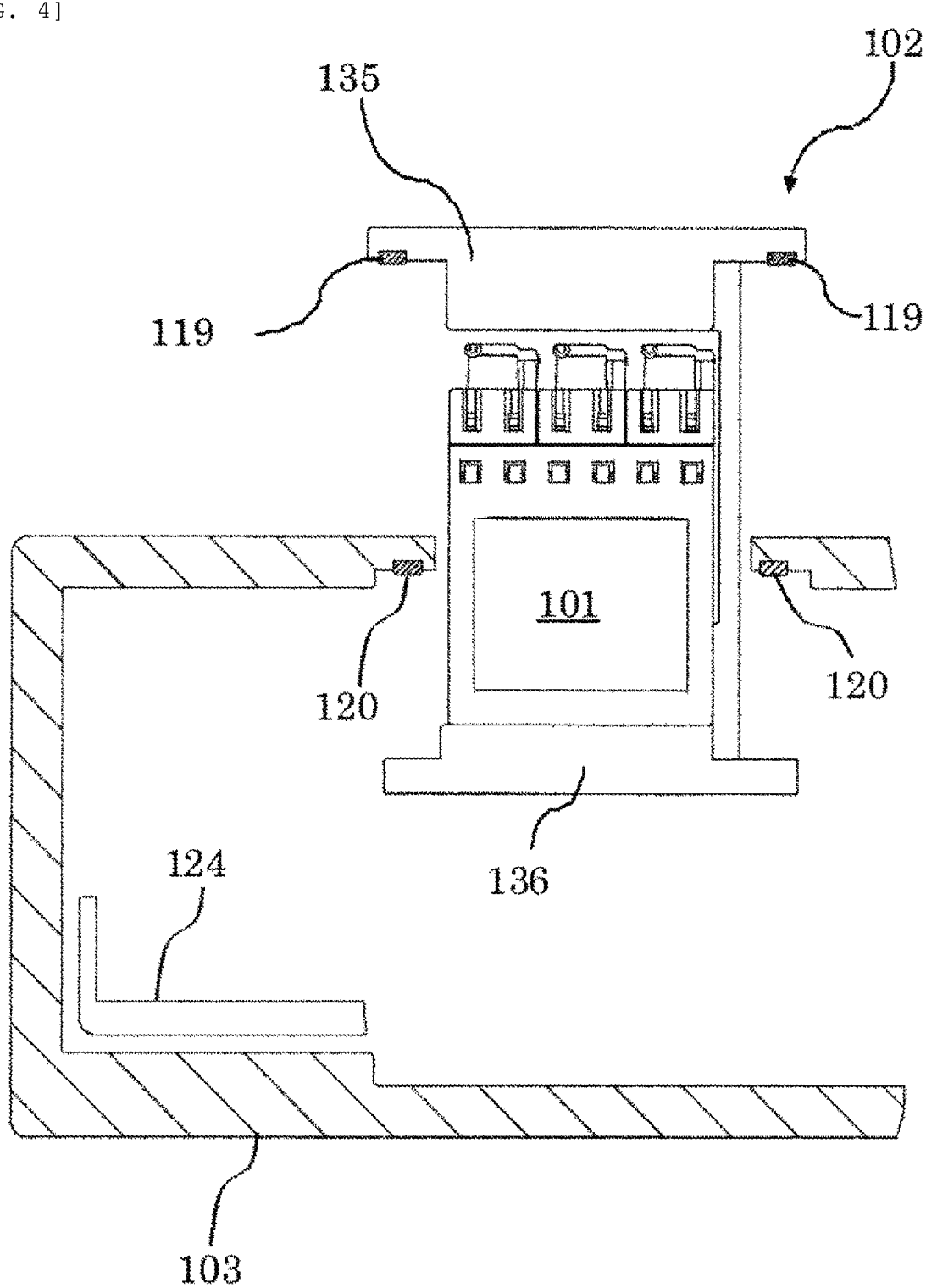

[FIG. 5-1]
(a)
STANDBY POSITION
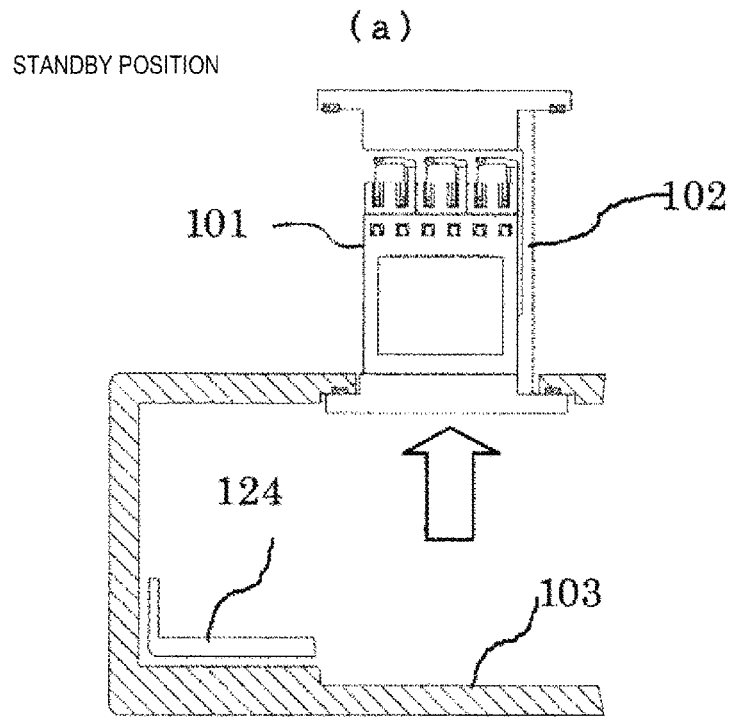
(b)
INTERMEDIATE POSITION
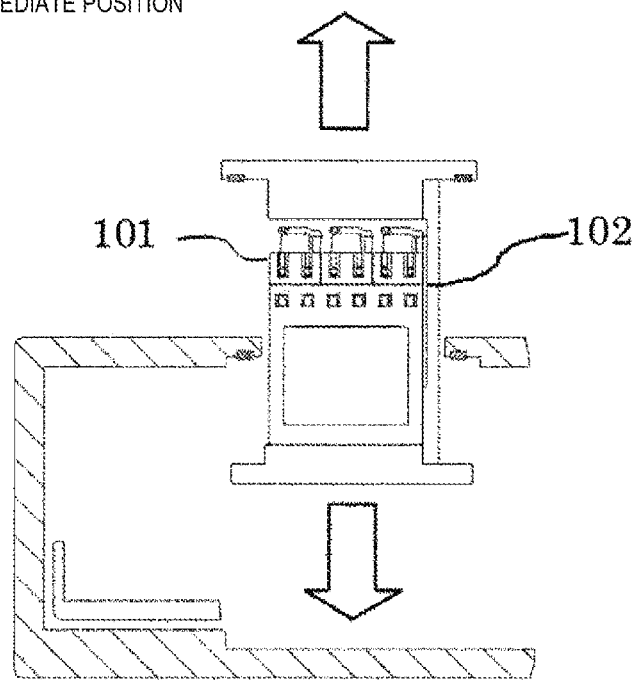

[FIG. 5-2]
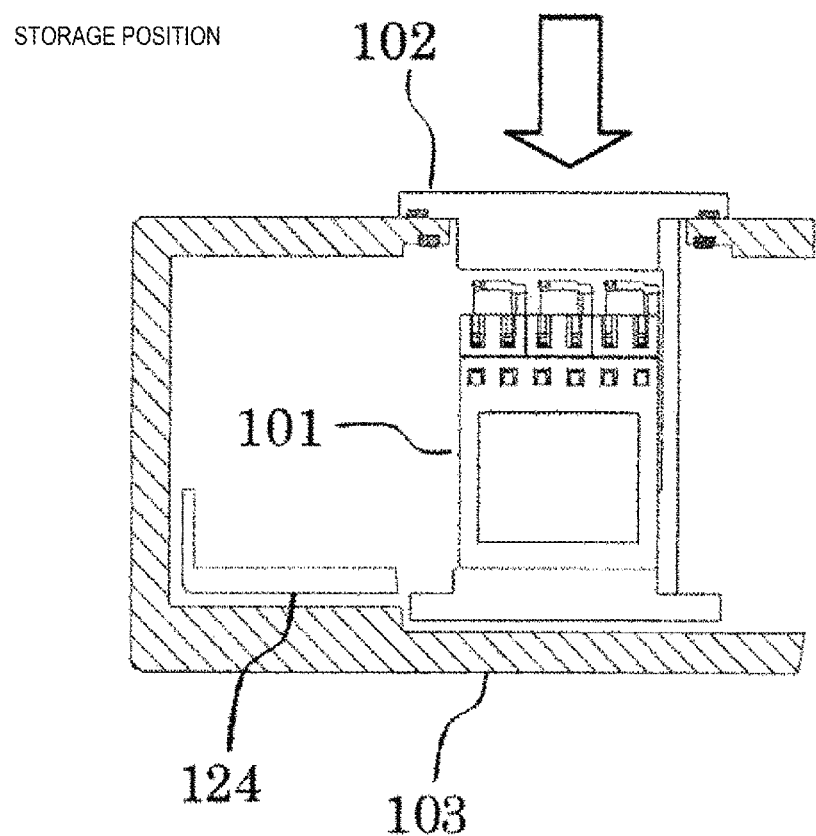

[FIG. 6]
(a)
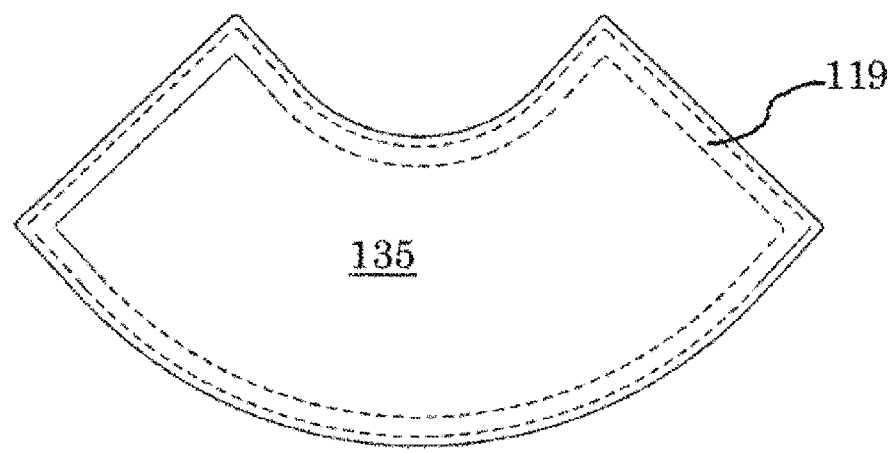
(b)
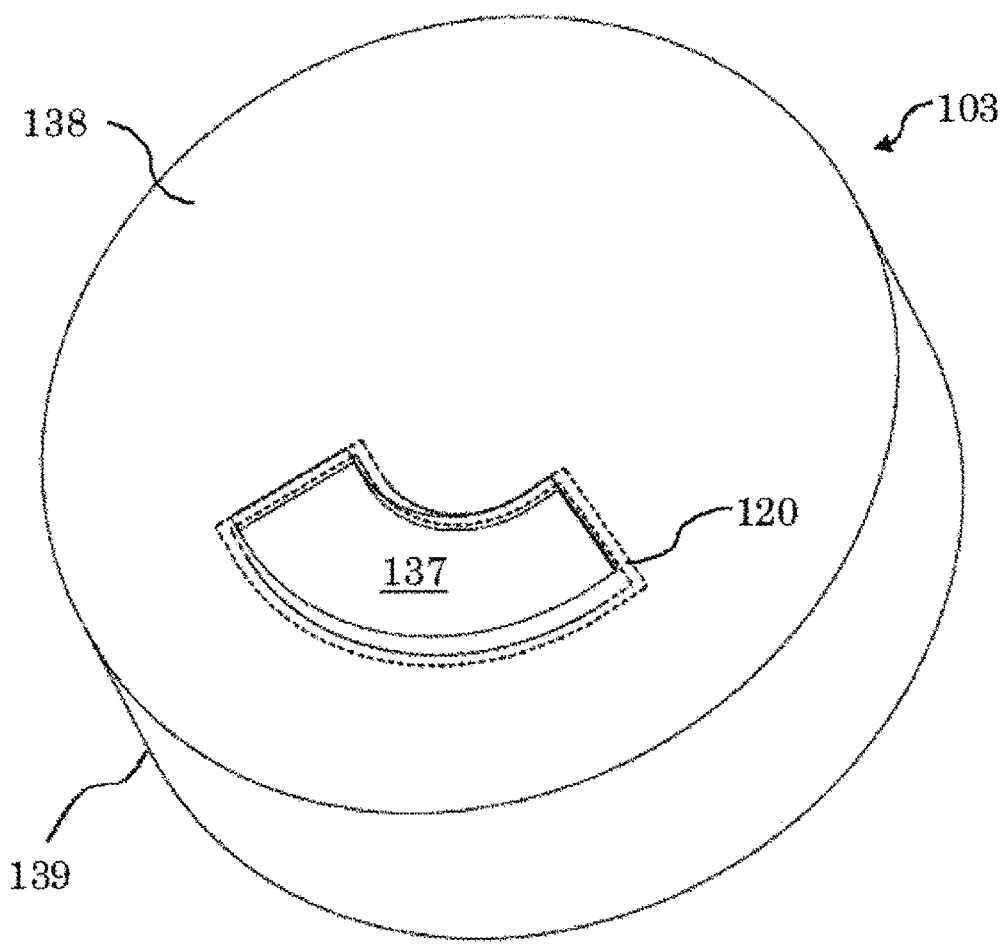

[FIG. 7]
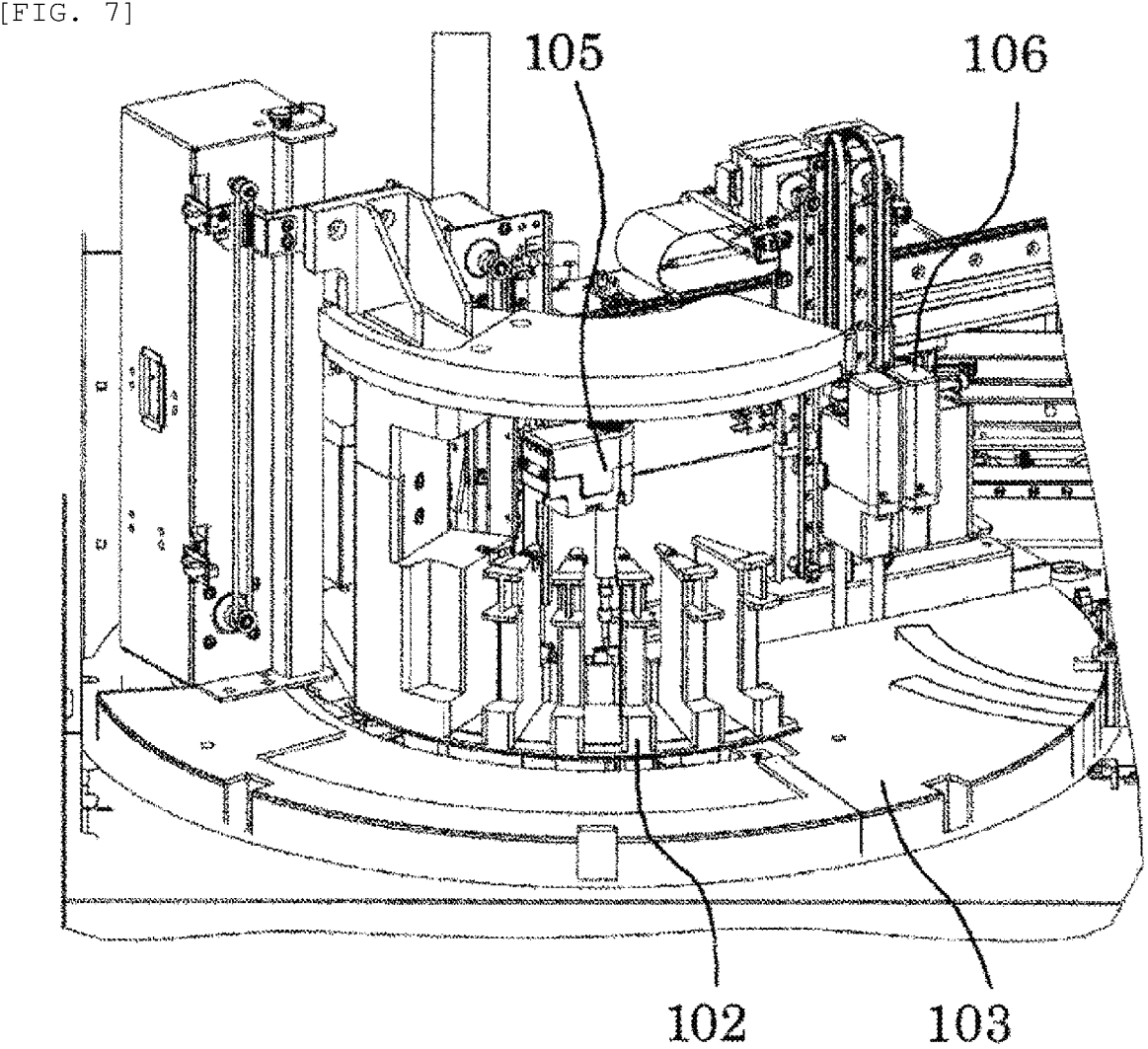

[FIG. 8]
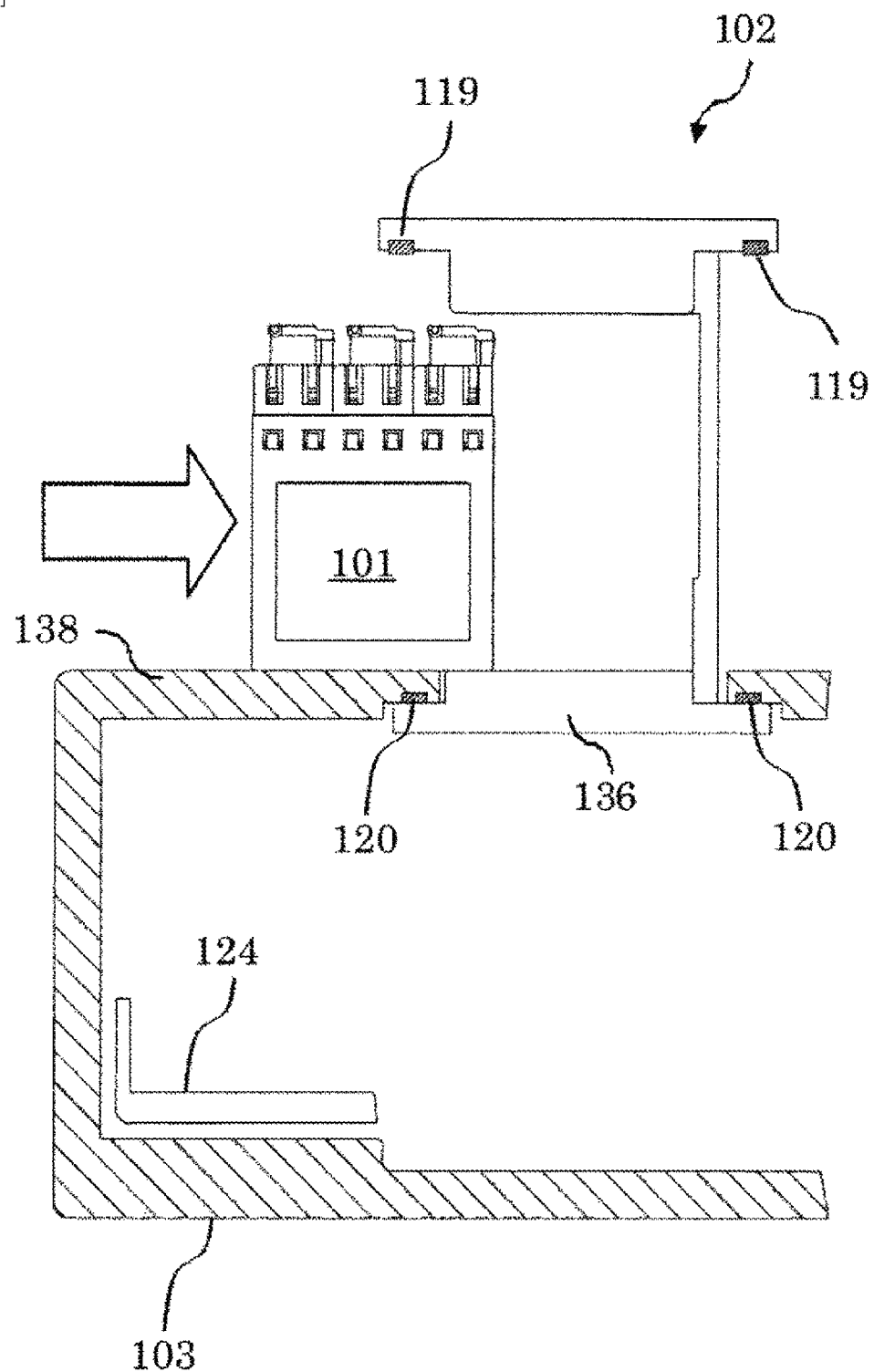

[FIG. 9]
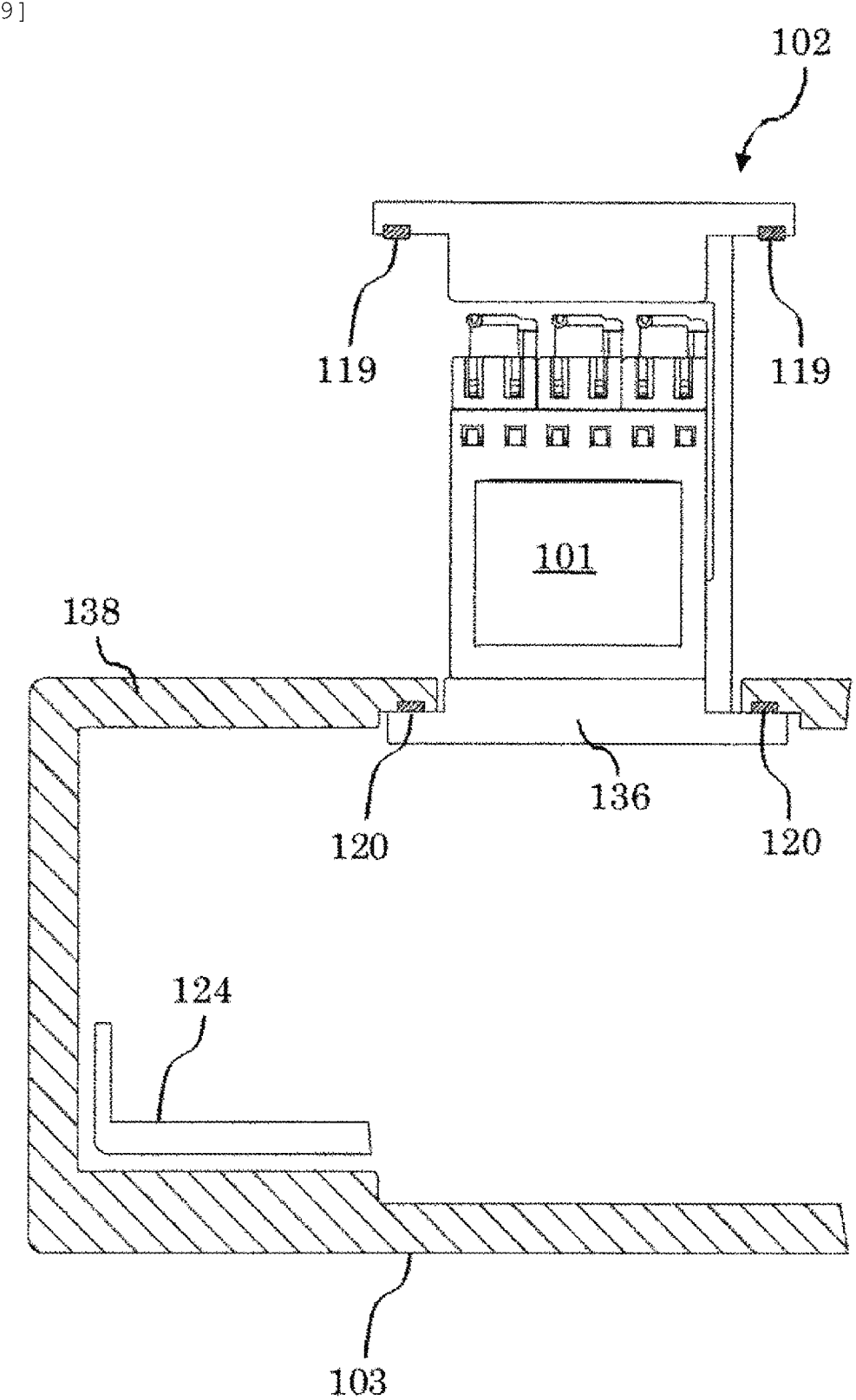

[FIG. 10]
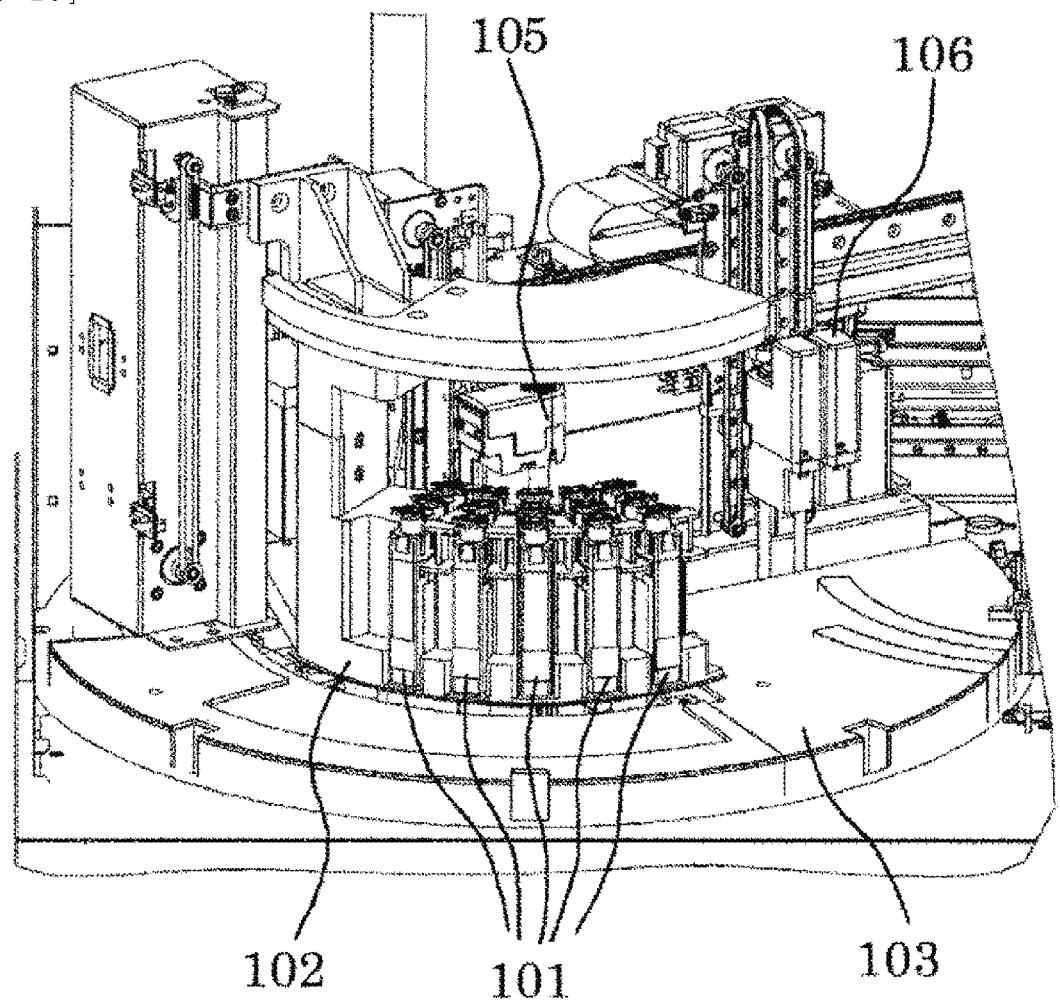

[FIG. 11]
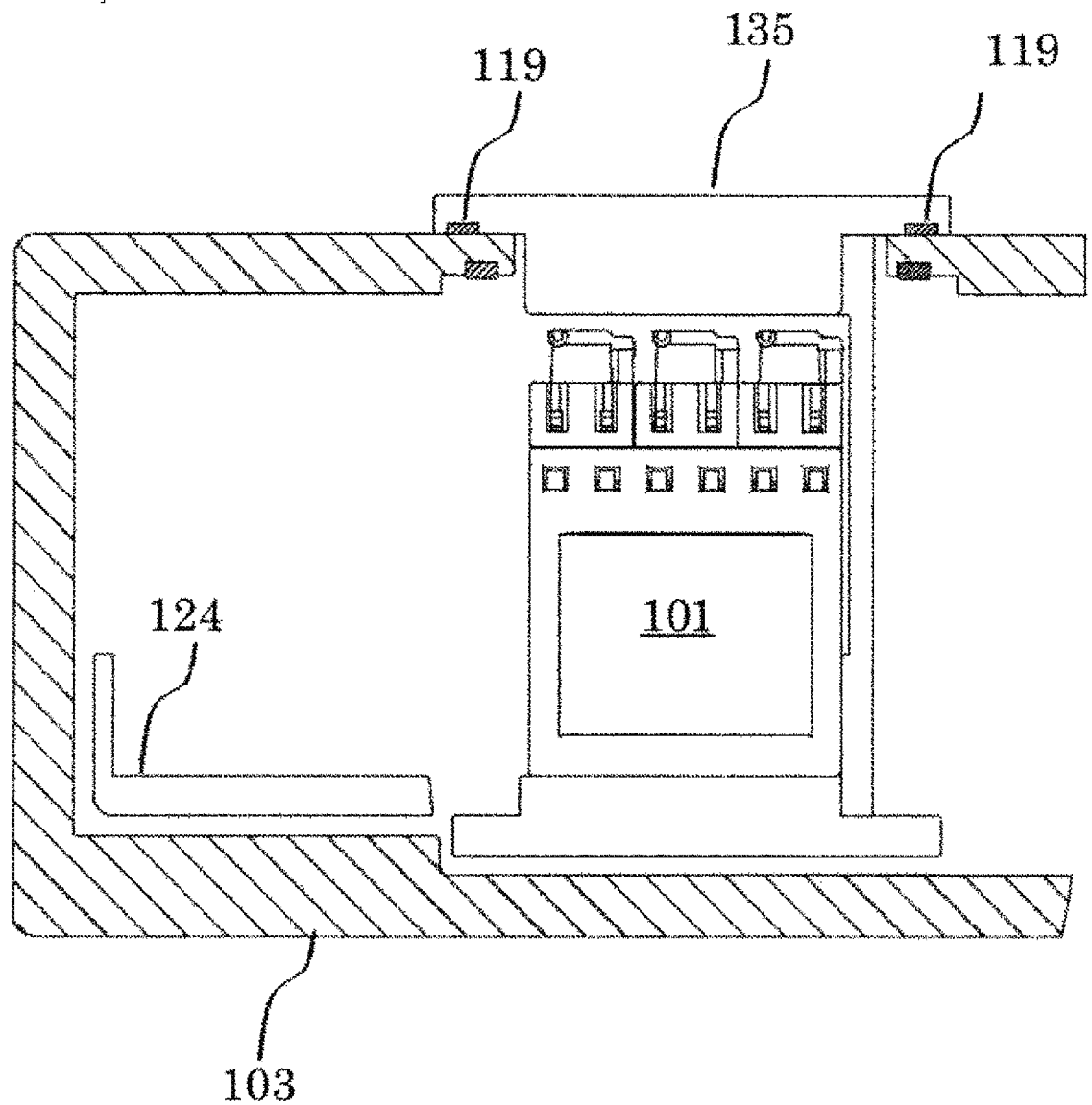

[FIG. 12]
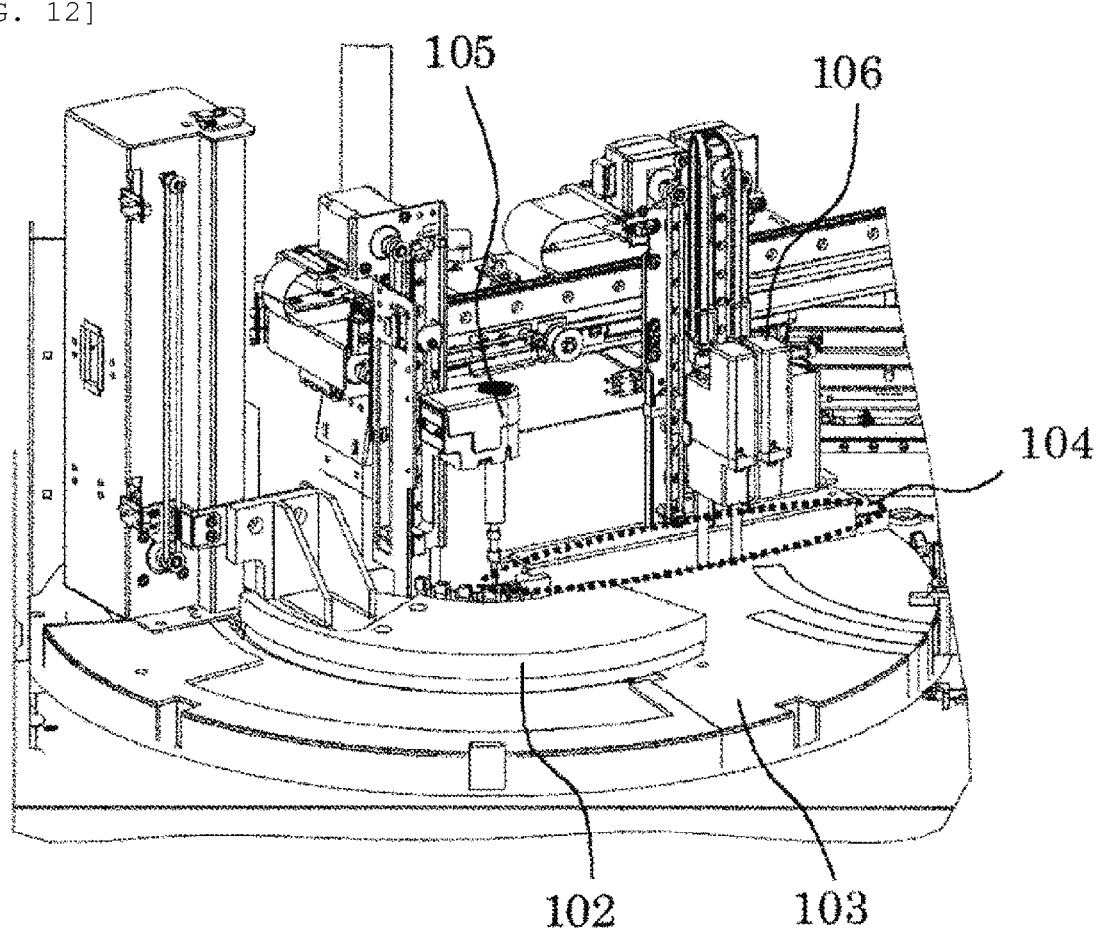

[FIG. 13]
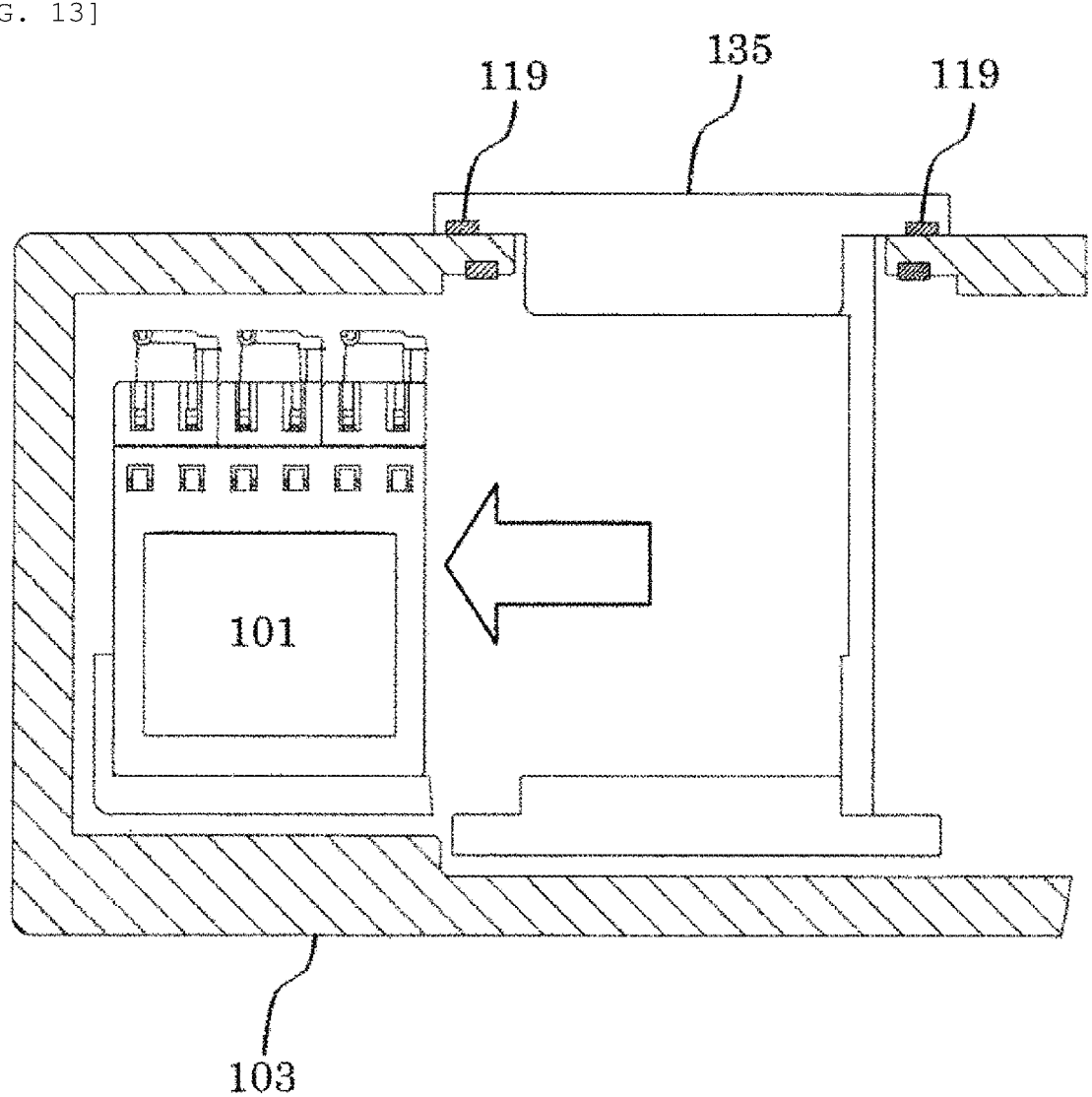

AUTOMATED ANALYZER

TECHNICAL FIELD

The present invention relates to an automated analyzer used for chemical analysis such as biochemical analysis or immunoassay in clinical tests.

BACKGROUND ART

It is known that an automated analyzer used for chemical analysis of biochemical analyzers, immunoassay analyzers, etc. in clinical tests includes a reagent storage chamber for storing a plurality of types of reagents (reagent containers) according to analysis items and cooling the stored reagent containers, and analyzes a reagent cooled in the reagent storage chamber (PTL 1).

PTL 1 describes an automated analyzer including a reagent-lid opening and closing mechanism capable of opening and closing a lid of the reagent container in the reagent storage chamber. In this analyzer, an operator puts the reagent into the reagent storage chamber in a state where an opening of the reagent container is sealed. The lid of the reagent container is automatically opened at the timing of using the reagent, so that it is possible to suck the reagent from the opening. Since the opening may be sealed again after using the reagent, it is possible to reduce the possibility of degradation of the reagent or leakage of the liquid.

CITATION LIST

Patent Literature

PTL 1: JP-A-2012-194071

SUMMARY OF INVENTION

Technical Problem

In the reagent storage chamber described in PTL 1, the inflow and outflow of heat occurs when a reagent container is unloaded from the reagent storage chamber. In order to prevent degradation due to a temperature change of a reagent, it is necessary to seal the reagent storage chamber as much as possible when the reagent container is loaded into and unloaded from the reagent storage chamber, and to prevent the entry and exit of air.

An object of the present invention is to provide an automated analyzer capable of reducing the temperature change in a reagent-container storage device, in the above-described reagent-container storage device.

Solution to Problem

The configuration of the present invention for solving the problem is as follows.

That is, an automated analyzer includes a storage chamber for adjusting the temperature of a container in which liquid is stored and storing the container, an opening provided in a portion of the storage chamber, and a loader mechanism for bringing the container in and out of the storage chamber by moving the container through the opening, and is characterized in that the loader mechanism and the storage chamber are closed by an elastic body.

Advantageous Effects of Invention

According to the present invention, since the inflow and outflow of heat into and from the outside and inside can be reduced even when the reagent container is loaded into and unloaded from the reagent storage chamber, it is possible to reduce variation in the storage temperature of the reagent in the reagent container. Consequently, it is possible to preserve the reagent for a lengthy period of time.

BRIEF DESCRIPTION OF DRAWINGS

FIG. 1 is a top view of the whole of an automated immunoassay analyzer of the present invention.

FIG. 2 is a perspective view illustrating a reagent loader mechanism of the invention.

FIG. 3 is a front view and a perspective view illustrating a reagent container.

FIG. 4 is a view illustrating a section of the reagent loader mechanism and a reagent storage chamber.

FIG. 5-1 is a view illustrating respective positions of the reagent loader mechanism.

FIG. 5-2 is a view illustrating respective positions of the reagent loader mechanism.

FIG. 6 is a view illustrating positions of sealing members of the reagent loader mechanism and the reagent storage chamber.

FIG. 7 is a view illustrating a state of the reagent loader mechanism in a standby position.

FIG. 8 is a view illustrating a state in which the reagent container is inputted to the reagent loader mechanism in the standby position.

FIG. 9 is a view illustrating a state in which the reagent container is inputted to the reagent loader mechanism in the standby position.

FIG. 10 is a view illustrating a state in which the reagent container is inputted to the reagent loader mechanism in the standby position.

FIG. 11 is a view illustrating a state of the reagent loader mechanism in a storage position.

FIG. 12 is a view illustrating a state in which the reagent loader mechanism is in the storage position.

FIG. 13 is a view illustrating a state in which the reagent container is moved from the storage position to a reagent refrigerator.

DESCRIPTION OF EMBODIMENTS

Hereinafter, an embodiment of the present invention will be described with reference to the drawings.

As an example of a device equipped with a reagent-container control mechanism 100 according to the present invention, the overall configuration and detection flow of an automated immunoassay analyzer will be described.

FIG. 1 is a top view illustrating the automated immunoassay analyzer as an example of the present invention.

The automated immunoassay analyzer mainly includes a reagent storage chamber 103 that includes a reagent loader mechanism 102 to automatically load and unload the reagent container 101 into and out of the chamber, a magnetic-particle stirrer 105 that stirs a reagent (especially reagent containing magnetic particles) in the reagent storage chamber 103, a magazine 127 that holds a plurality of expendables (for example, a reaction container and a specimen dispensing chip) required for analysis, a reaction container/specimen dispensing chip carrier 128 that conveys the expendables on the magazine 127 to appropriate positions, a specimen dispenser 129 that dispenses a predetermined amount from specimens 133 on a conveyance line to the reaction container in a state where the specimen dispensing chip is attached, a reaction tank 108 that keeps the reaction container containing the specimen at a predetermined temperature, a reagent dispenser 106 that sucks a predetermined amount of reagent in the reagent storage chamber 103 and discharges it into the reaction container, a reaction-liquid stirrer 121 that stirs the sample and the reagent in the reaction container to mix them with each other, and a reaction-liquid cleaning device 122 that removes components other than components to be measured in the reaction container, and a detection unit 123 that quantitatively measures the components to be measured in the reaction liquid.

The reagent storage chamber 103 accommodates a reagent disk including a plurality of slots to hold the reagent containers, in a housing including an opening in an upper part thereof. The reagent disk may rotationally move any of the reagent containers and then position the reagent container to a desired position. The opening of the housing is sealed by a lid (not illustrated). A plurality of passages through which the reagent loader mechanism 102, a stirrer of the magnetic-particle stirrer 105 and a probe of the reagent dispenser 106 may pass is provided, respectively, on a portion of the lid.

A reagent-container moving device 125 is accommodated in the reagent storage chamber 103 to be rotatable in a circumferential direction while being stretchable in a diametric direction of the reagent storage chamber. The reagent container 101 may be moved between the reagent loader mechanism 102 and the slot of the reagent disk 124 and between the stirring position by the magnetic-particle stirrer 105 and the slot of the reagent disk 124.

A reagent-container-lid opening and closing device 126 is also accommodated in the reagent storage chamber 103. Before being treated by the magnetic-particle stirrer 105 or the reagent dispenser 106, the lid of the reagent container 101 is opened at an appropriate timing so that the stirrer and the dispenser may access the reagent in the reagent container. When treatment has been completed, the lid is closed after the use of the reagent, thus preventing the degradation of the reagent. The structure is not particularly limited, and it is possible to adopt a known configuration capable of automatically opening and closing the lid of the reagent container. In the case where the reagent-container-lid opening and closing device 126 may release the reagent container lid from the sealed state, it is unnecessary to provide a half opener in a reagent input unit 100.

First, as preparations before the start of analysis, in order to install the reagent container 101 used for analysis on the reagent disk 124 in the reagent storage chamber 103, an operator installs the reagent container 101 in the reagent loader mechanism 102 via the reagent-container input unit 100.

Thereafter, an input operation is performed by an instruction button so that the reagent loader mechanism 102 is moved down and into the reagent storage chamber 103. The reagent container 101 placed on the reagent loader mechanism 102 is moved to an empty slot of the reagent disk 124 by the reagent-container moving device 125. The reagent container 101 moved to the reagent disk 124 is used for an analysis process after an appropriate preparation process is performed.

The magnetic-particle stirrer 105, the reagent dispenser 106, and the like are provided outside the reagent storage chamber 103, and may make access to the reagent container 101 mounted on the reagent disk 124 at a stirring dispensing position 104.

The reagent disk 124 may be rotationally driven in a horizontal direction, so that, in the analysis process, the mounted reagent container 101 is moved to the stirring dispensing position 104, and a lid portion of the reagent container 101 is opened by the reagent-container-lid opening and closing device 126, the magnetic-particle stirrer 105 stirs the magnetic particles in the reagent container 101, and the reagent dispenser 106 sorts and dispenses the reagent contained in the reagent container 101. When the stirring of the magnetic particles, the sorting of the reagents, and the dispensing have been completed, the lid portion of the reagent container 101 may be closed by the reagent-container-lid opening and closing device 126.

In the analysis process, first, a new reaction container mounted on the magazine 127 is transferred into the reaction tank 108 by the reaction container/specimen dispensing chip carrier 128, and a new specimen dispensing chip is transferred to a position where it is attached to a tip of the probe of the specimen dispenser 129. The reaction tank 108 may be horizontally rotated while holding a plurality of reaction containers, and the reaction tank 108 is rotated to the reagent dispensing position, and the reagent in the reagent container 101 is first dispensed into the reaction container. Since the process performed until the reagent in the reagent container 101 is dispensed is described in first embodiment, it will be omitted. Simultaneously, the specimen dispenser 129 equipped with the specimen dispensing chip sucks the specimen mounted on a specimen rack 107 and moves the reagent dispensed reaction container to the specimen dispensing position by the rotation of the reaction tank 108, and the dispenser 129 dispenses the specimen into the reaction container. Thereafter, in order to cause the reagent and the specimen to react with each other in the reaction container, a temperature is maintained for a predetermined period of time on the reaction tank 108.

Thereafter, the reaction container moves again to the reagent dispensing position, and the magnetic particles in the reagent container 101 are dispensed by the reagent dispenser 106. Then, after the reaction tank 108 rotates, the reaction container on the reaction tank 108 is moved to the reaction-liquid stirrer 121 by the reaction container/specimen dispensing chip carrier 128, and the magnetic particles, the reagent and the specimen reacting with each other for a predetermined period of time are stirred by the reaction-liquid stirrer 121. The reaction container that has been stirred returns to the reaction tank 108 again by the reaction container/specimen dispensing chip carrier 128, further reacts for a predetermined period of time on the reaction tank 108, and then the reaction liquid (reagent/specimen/magnetic particles) in the reaction container flows into the detection unit 123 to performs detection. Depending on the item to be analyzed, for the purpose of removing impurities from the reaction liquid before the detection, the reaction-liquid cleaning device 122 may clean the reaction liquid. The series of processes may be carried out continuously.

FIG. 2 is a perspective view illustrating the surroundings of the reagent loader mechanism 102 of the automated analyzer according to the first embodiment of the present invention. Originally, a cover is provided to prevent access by the operator during the analysis operation from the upper surface to the front surface of the analyzer. In order to make it easy to see mechanism parts related to the present invention, the cover is omitted in all the drawings. Further, although the automated analyzer using the magnetic-particle reagent for analyzing a sample is described as an example, there is no particular limitation on the type of reagent and the like.

The reagent storage chamber 103 in the automated analyzer to which the present invention is applied has a cold reserving function. The reagent storage chamber 103 is provided with a reagent loader mechanism 102 capable of installing a plurality of sets of reagent containers 101, a reagent-container input unit 100, and a reagent loader cover 107. The operator may load the reagent container into the reagent loader mechanism 102 at an appropriate angle and position by sliding the reagent container along a reagent input guide 130 of the reagent-container input unit 100. When the reagent container is not put into and out of the reagent loader mechanism 102, it is possible to prevent foreign matter from being caught in the reagent loader mechanism 102 by closing the reagent loader cover 107.

The reagent-container input unit 100 is provided above the lid of the reagent storage chamber 103 and before the reagent loader mechanism 102. The reagent-container input unit 100 includes the reagent input guide 130 and the half opener 131. The reagent input guide 130 is disposed on a path for putting the reagent container into the slot 132 of the reagent loader mechanism 102 and is disposed adjacent to the slot of the reagent loader mechanism 102. When the reagent container is loaded into the reagent loader mechanism 102, it comes into contact with a portion of a bottom surface and a side surface of the reagent container so that the reagent container is loaded into the reagent loader mechanism 102 at a correct angle and position. In the present embodiment, a groove portion (recessed portion) in which the reagent container is installed and blocks (protruding portions) arranged on both sides of the groove portion are formed, but the present invention is not limited to this embodiment. Further, when the reagent is loaded into the reagent loader mechanism 102 by the reagent input guide 130, the half opener 131 may be brought into contact with a reagent container lid provided on the upper portion of the reagent container to change the lid from the closed state into a half-opened state.

The reagent loader mechanism 102 includes the plurality of slots 132 that hold the reagent container to load and unload it into and out of the reagent storage chamber 103. In order to slide the reagent container into and out of the reagent-container moving device 125 in the reagent storage chamber 103, each slot 132 of the reagent loader mechanism 102 is provided at the same angle as the slot of the reagent disk arranged along a circumference. Further, a motor (not illustrated) for moving the reagent loader mechanism 102 in a vertical direction is provided so that the reagent container may be moved between the inside of the reagent storage chamber and the lid of the reagent storage chamber. Furthermore, an instruction button is provided to allow the operator to instruct to drive the reagent loader mechanism 102. The vertical movement of the reagent loader mechanism 102 may be performed from a screen for operating the automated analyzer.

FIG. 3 is an example of the reagent container 101 applied to the present invention.

The reagent container 101 is configured such that a plurality of reagents used for one analysis is set as one set. For example, in FIG. 3, the reagent container has a shape in which three reagent receiving parts 133 are set as one set. The upper portion of each reagent receiving part includes an opening to which the openable lid 134 is attached, so that it may be opened and closed by the afore-mentioned reagent-container-lid opening and closing device 126. Although the method of attaching the lid is not particularly limited, in FIG. 3, it is possible to open and close the opening by rotating and lifting the other end about one end of the lid as a rotation axis. It is preferable that a barcode label or an RFID tag is attached to the side surface of the reagent container as a storage medium in which information on measurement performed using the reagent or the reagent contained therein is stored.

FIG. 4 is a sectional view of the reagent loader mechanism 102 according to the present invention.

The reagent loader mechanism includes a reagent-loader lid 135 and a reagent loader base 136 as closing members that are arranged vertically to be spaced apart from each other. The reagent-loader lid 135 and the reagent loader base 136 have areas sufficiently larger than that of the opening 137 provided in a reagent cold reserving lid to allow the reagent loader mechanism 102 to pass therethrough. Therefore, in a state where the reagent loader mechanism 102 is in a storage position (a state where the reagent loader mechanism is in the lowermost position, namely, a state where the reagent container may be loaded and unloaded into and out of the reagent storage chamber) or a state where the reagent loader mechanism is in the standby position (a state where the reagent loader mechanism is in the uppermost position, namely, a state where the operator may load and unload the reagent container into and out of the reagent loader mechanism 102), it is possible to completely cover the opening 137.

Further, a sealing member 119 made of an elastic body is provided on the lower surface of the reagent-loader lid 135, and is in contact with the upper surface of the reagent-storage-chamber lid in the state where the reagent loader mechanism 102 is in the storage position, thus sealing the opening through which the reagent loader mechanism passes. In addition, the reagent loader base 136 has a plane larger than the opening through which the reagent loader mechanism passes, and is in contact with a sealing member 120 made of an elastic body having an upper surface provided on the lower surface of the reagent-storage-chamber lid, in the state where the reagent loader mechanism 102 is in standby position, thus sealing the opening through which the reagent loader mechanism passes. For example, nitrile rubber, fluoro rubber, urethane rubber, silicone rubber, ethylene propylene rubber, chloroprene rubber, hydrogenated nitrile rubber and the like may be used as the elastic body, and rubber or rubber foam excellent in weather resistance and chemical resistance may be used.

FIGS. 5-1, and 5-2 are views illustrating possible states of the reagent loader mechanism according to the present invention.

First, the state where the reagent loader mechanism is in the standby position is illustrated in (a) of FIG. 5-1. The standby position is a position where the operator may put or take the reagent container into or out from the reagent loader mechanism, specifically, a state where the reagent loader mechanism 102 is on the reagent-storage-chamber lid.

Next, by detecting an instruction from the operator or a predetermined trigger, the reagent loader starts to descend and is located at an intermediate position illustrated in (b) of FIG. 5-1. At the intermediate position, if necessary, information of a reagent identifier such as a bar code or an RFID tag attached to the reagent container 101 may be read. Especially when there is no reading information, the reagent loader continues to descend without doing anything in the intermediate position.

Subsequently, the reagent loader mechanism 102 may further descend to be positioned at a storage position illustrated in (c) of FIG. 5-2. The storage position is a state where the reagent loader mechanism with the reagent container 101 mounted thereon descends and is accommodated in the reagent storage chamber, specifically, the reagent loader mechanism 102 is stored in the reagent storage chamber. A reagent-container moving mechanism may access the reagent container on the reagent loader mechanism 102 in this state and thereby move the reagent container.

FIG. 6 is a view illustrating the arrangement of the sealing members around the reagent loader mechanism in the present invention.

On the lower surface of the reagent-loader lid 135 of the reagent autoloader mechanism 102, a sealing member 119 is provided in a region surrounded by a dotted line in the drawing. The sealing member 119 has a shape that surrounds the outer periphery of the opening 137 provided in the reagent-loader lid 102. According to this embodiment, since the opening 137 has a fan shape, the elastic body 119 has a fan shape that is slightly larger than the opening 137.

Likewise, the sealing member 120 disposed on the lower surface of the reagent-storage-chamber lid is arranged to surround the opening provided in the reagent-storage-chamber lid. By providing the sealing members 119 and 120 that surround the circumference of the reagent-loader lid and the opening of the reagent-storage-chamber lid in this manner, the opening may be hermetically sealed in a state where the reagent loader mechanism is raised and lowered, thus preventing heat from escaping from the reagent storage chamber or entering from the outside while keeping the internal temperature of the storage chamber constant. In the case of shortening the time existing in the reagent standby position, the elastic body 120 may not be provided.

FIGS. 7 to 10 are views illustrating the arrangement relationship between the reagent loader mechanism and the reagent storage chamber in the standby position.

In the state where the reagent loader mechanism 102 is in the standby position, as illustrated in FIG. 8, the opening 137 is covered by the reagent loader base. Further, when the sealing member 120 provided on the lower surface of the reagent-storage-chamber lid 138 is pressed against the upper surface of the reagent loader base 136, a gap between the reagent loader base and the reagent-storage-chamber lid is hermetically sealed, thus preventing temperature fluctuations due to the inflow and outflow of air in the reagent storage chamber 103.

In this state, the operator puts the reagent container 101 into the slot 132 of the reagent loader mechanism 102 by sliding the reagent container over the reagent container guide 100. Since the sealing member is not present in the path through which the reagent container 101 slides, the sealing member is not abraded and thereby the sealing performance is not deteriorated due to the contact of the bottom surface of the reagent container 101 with the sealing member.

It is preferable that the reagent container guide 100 and the reagent loader base 136 be smoothly connected in a state where the reagent loader mechanism is in the standby position. According to this embodiment, the reagent-storage-chamber lid 138 has a thin region that is formed around the opening 137 so that the reagent loader base abuts thereon. Likewise, the reagent loader base 136 has a thin region that is formed around the outer periphery thereof so that the reagent-storage-chamber lid 138 abuts thereon. In the standby state, the thin regions of the reagent-storage-chamber lid 138 and the reagent loader base 136 overlap so that the surface of the reagent-loader lid 136 coming into contact with the bottom surface of the reagent container 101 is smoothly connected from the reagent container guide 100 and consequently the reagent container may move smoothly without being caught by other components. The elastic body 120 is provided in the thin region of the reagent-storage-chamber lid 138.

FIGS. 11 to 13 are views illustrating the arrangement relationship between the reagent loader mechanism and the reagent storage chamber in the storage position.

In the state where the reagent loader mechanism 102 is in the storage position, as illustrated in FIG. 11, the opening 137 is covered by the reagent-loader lid 135. Further, the sealing member 119 provided on the lower surface of the reagent loader lid abuts on the upper surface of the reagent-storage-chamber lid 138 to close the gap between the opening 137 and the reagent-loader lid 135 while preventing air from flowing into and out of the reagent storage chamber.

In this state, the reagent container moving mechanism 125 accesses the reagent container 101 and slidably moves from the slot on the reagent loader mechanism 102 to the empty slot on the reagent disk 124. Since the sealing member is not present in the path through which the reagent container 101 slides, the sealing member is not abraded and thereby the sealing performance is not deteriorated due to the contact of the bottom surface of the reagent container 101 with the sealing member.

According to this embodiment, in both the standby position where the reagent container 101 may be installed in the reagent loader mechanism 102 from the outside and the storage position where the reagent container 101 may be installed in the reagent storage 103 from the reagent loader mechanism 102, since the opening provided in the reagent storage chamber 103 is hermetically sealed, it is possible to prevent the inflow and outflow of heat from the reagent storage chamber while providing a large-sized reagent loader mechanism capable of loading and unloading a plurality of reagent containers at the same time.

Further, since the sealing members are provided on the lower surface of the reagent-storage-chamber lid and the lower surface of the reagent-loader lid, the accumulation of dust and the deterioration of the sealing performance are never generated even if they are used for a lengthy period of time.

Although the reagent storage chamber of the type in which the reagent containers are arranged on the circumference is described as an example in this embodiment, the present invention is not limited thereto. For example, it may be a reagent storage chamber in which a plurality of reagent containers is arranged and stored in a row, or a reagent storage chamber in which reagent containers are arranged in the form of an array.

In the present embodiment, the automated immunoassay analyzer has been explained as an example. However, the present application is not limited to this, and other analyzers such as an automated biochemical analyzer, an automated coagulation analyzer or an automated scattering analyzer may be used as long as they are devices that perform analysis using refrigerated reagents.

Further, the invention is not limited to the reagent storage chamber, but any other storage chambers may be used as long as they are storage chambers in which a container containing liquid is temperature-controlled and stored. For example, it may be a thermostatic bath or an incubator that stores sample containers.

Further, the reagent loader mechanism is not limited to being driven vertically with respect to the reagent storage chamber, but it may be moved horizontally to load and unload reagent containers.

REFERENCE SIGNS LIST

100: reagent-container input unit
101: reagent container

102: reagent loader mechanism
103: reagent storage chamber
104: stirring dispensing position
105: magnetic-particle stirrer
106: reagent dispenser
107: specimen rack
108: reaction tank
119: sealing member (reagent loader mechanism)
120: sealing member (reagent storage chamber)
121: reaction-liquid stirrer
122: reaction-liquid cleaning device
123: detection unit
124: reagent disk
125: reagent-container moving device
126: reagent-container-lid opening and closing device
127: magazine
128: reaction container/specimen dispensing chip carrier
129: specimen dispenser
130: reagent input guide
131: half opener
132: slot
133: reagent storage part
134: reagent lid
135: reagent loader lid
136: reagent loader base
137: opening
138: reagent-storage-chamber lid
139: housing

The invention claimed is:

1. An automated analyzer comprising:
a storage chamber for adjusting the temperature of a container in which liquid is stored and storing the container;
an opening provided in a portion of the storage chamber; and
a loader mechanism for loading and unloading the container to positions inside of and outside the storage chamber by moving the container into and out of the storage chamber via the opening, wherein
the loader mechanism is configured to move from a lower position to an upper position relative to a gravity direction and relative to the storage chamber to move the container from the position inside of the storage chamber to the position outside of the storage chamber,
the loader mechanism is configured to move from the upper position to the lower position relative to the gravity direction and relative to the storage chamber to move the container from the position outside of the storage chamber to the position inside of the storage chamber,
the loader mechanism includes a first closing member configured to close the opening when the loader mechanism is in the lower position and a second closing member configured to close the opening when the loader mechanism is in the upper position,
the first closing member or the storage chamber includes a first elastic body configured to seal an outer periphery of the opening along an outside surface of the storage chamber by being pressed between the first closing member and the storage chamber,
the storage chamber includes a second elastic body configured to seal the outer periphery of the opening along an inside surface of the storage chamber by being pressed between the second closing member and the storage chamber,
the second elastic body is disposed at an upper wall of the storage chamber having a reduced thickness region, said reduced thickness region being configured to permit movement of the container into the loader mechanism when the loader mechanism is in the upper position and said reduced thickness wall region configured to permit sliding movement of the container out of the loader mechanism past the second elastic body within the storage chamber without contact between the second elastic body and the container when the loader mechanism is in the lower position; and
the first closing member has a reduced thickness region configured to overlap with the reduced thickness region of the storage chamber upper wall.

2. The automated analyzer of claim 1, wherein
the first elastic body has a shape of substantially surrounding the outer periphery of the opening, and
the second elastic body has a shape substantially surrounding the outer periphery of the opening.

3. The automated analyzer of claim 1, wherein
the container is a reagent container that accommodates a reagent used for analysis, and
the storage chamber is a reagent storage chamber that accommodates a reagent disk including a plurality of slots capable of storing a plurality of reagent containers.

4. The automated analyzer of claim 1, wherein
the opening is provided in a portion of an upper surface of the storage chamber, and the loader mechanism moves vertically through the opening.

5. The automated analyzer of claim 4,
wherein the first elastic body is provided on a lower surface of the first closing member, and the second elastic body is provided on a lower surface of a region inside of the storage chamber around the opening.

6. The automated analyzer of claim 1, wherein
each of the first and second closing members has an area larger than an area of the opening.

* * * * *